United States Patent
Flexman et al.

(10) Patent No.: US 11,969,221 B2
(45) Date of Patent: Apr. 30, 2024

(54) MULTIPURPOSE LUMEN DESIGN FOR OPTICAL SHAPE SENSING

(71) Applicant: KONINKLIJKE PHILIPS N.V., Eindhoven (NL)

(72) Inventors: Molly Lara Flexman, Boston, MA (US); David Paul Noonan, New York, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/961,923

(22) Filed: Apr. 25, 2018

(65) Prior Publication Data

US 2018/0235717 A1    Aug. 23, 2018

Related U.S. Application Data

(62) Division of application No. 15/022,078, filed as application No. PCT/IB2014/064538 on Sep. 16, 2014, now Pat. No. 9,974,617.

(Continued)

(51) Int. Cl.
| | |
|---|---|
| *A61B 5/00* | (2006.01) |
| *A61B 5/107* | (2006.01) |
| *A61B 17/00* | (2006.01) |
| *A61B 34/00* | (2016.01) |
| *A61B 34/20* | (2016.01) |

(Continued)

(52) U.S. Cl.
CPC ............ *A61B 34/20* (2016.02); *A61B 5/1076* (2013.01); *A61B 5/6852* (2013.01); *A61B 34/71* (2016.02); *G02B 23/2469* (2013.01); *G02B 23/2476* (2013.01); *A61B 2017/00199* (2013.01); *A61B 2017/00323* (2013.01); *A61B 2017/00845* (2013.01); *A61B 2034/2061* (2016.02); *A61B 2562/0266* (2013.01); *A61M 25/0026* (2013.01);

(Continued)

(58) Field of Classification Search
CPC .. A61B 17/00; A61B 5/00; A61B 1/00; A61B 34/20; A61B 18/14; A61B 18/20; A61B 34/71; A61B 5/1076; A61B 5/6852; A61B 2017/00323; A61B 2034/2061; A61M 25/00; A61M 25/01; A61M 25/0026
See application file for complete search history.

(56) References Cited

U.S. PATENT DOCUMENTS 6,004,310 A * 12/1999 Bardsley ........... A61M 25/0009
                                                    604/524
7,329,223 B1 * 2/2008 Ainsworth ........... A61B 5/0084
                                                    600/300

(Continued)

FOREIGN PATENT DOCUMENTS

WO      2013056006 A2    4/2013

*Primary Examiner* — Omar R Rojas

(57) ABSTRACT

A shape sensing enabled instrument includes a flexible guide wire or support rod including an outer surface which encapsulates interior features. The interior features include an optical fiber lumen (105) configured to receive one or more optical fibers for optical shape sensing, and a guide wire support rod or the support rod forming a hollow extending longitudinally along the instrument. The guide wire support rod or the support rod is configured to receive the optical fiber lumen therein to permit rotation and translation of an optical fiber and to protect the optical fiber.

15 Claims, 3 Drawing Sheets

Related U.S. Application Data

(60) Provisional application No. 61/884,161, filed on Sep. 30, 2013.

(51) Int. Cl.
  *A61M 25/00* (2006.01)
  *G02B 23/24* (2006.01)
  *A61M 25/01* (2006.01)
  *A61M 25/09* (2006.01)

(52) U.S. Cl.
  CPC ... *A61M 25/0102* (2013.01); *A61M 2025/091* (2013.01); *A61M 2025/0915* (2013.01)

(56) References Cited

U.S. PATENT DOCUMENTS

| | | | |
|---|---|---|---|
| 7,572,257 B2 | 8/2009 | Whayne et al. | |
| 8,050,523 B2 | 11/2011 | Younge et al. | |
| 8,633,433 B2 | 1/2014 | Yasuda et al. | |
| 8,705,903 B2 | 4/2014 | Younge et al. | |
| 8,781,275 B2 | 7/2014 | Asselin et al. | |
| 8,957,367 B2 | 2/2015 | Prisco et al. | |
| 2003/0013985 A1 | 1/2003 | Saadat | |
| 2006/0013523 A1 | 1/2006 | Childlers et al. | |
| 2006/0030753 A1* | 2/2006 | Boutillette | A61B 1/0057 600/146 |
| 2007/0225559 A1 | 9/2007 | Clerc et al. | |
| 2008/0039715 A1* | 2/2008 | Wilson | A61B 5/06 600/424 |
| 2011/0151980 A1 | 6/2011 | Petroff | |
| 2011/0254938 A1* | 10/2011 | Asada | A61B 1/041 348/76 |
| 2012/0027351 A1 | 2/2012 | Asselin et al. | |
| 2013/0204124 A1 | 8/2013 | Duindam et al. | |
| 2015/0080743 A1* | 3/2015 | Siess | A61B 5/02154 600/478 |
| 2015/0209117 A1 | 7/2015 | Flexman et al. | |

* cited by examiner

MULTIPURPOSE LUMEN DESIGN FOR OPTICAL SHAPE SENSING

CROSS-REFERENCE TO PRIOR APPLICATIONS

This is a divisional of prior application Ser. No. 15/022,078 filed Mar. 16, 2016. Application Ser. No. 15/022,078 is a U.S. National Phase application under 35 U.S.C. § 371 of International Application Serial No. PCT/IB2014/064538, filed on Sep. 16, 2014, which claims the benefit of U.S. Application Serial No. 61/884,161, filed on Sep. 30, 2013. These applications are hereby incorporated by reference herein.

BACKGROUND

Technical Field

This disclosure relates to optical shape sensing instruments and more particularly to a lumen for use with shape sensing optical fibers which protects and permits rotation of the optical fibers.

Description of the Related Art

Optical shape sensing (OSS) uses light along a multicore optical fiber for device localization and navigation during surgical intervention. Shape sensing based on fiber optics exploits the inherent backscatter in a conventional optical fiber. The principle involved makes use of distributed strain measurement in the optical fiber using characteristic Rayleigh backscatter or controlled grating patterns.

Integrating an optical shape sensing fiber into a medical device can provide localization information for use during navigation inside the body. Many interventional devices have small cross-sectional footprints that limit the amount of space available for including an optical fiber. In addition, the manner in which the fiber is integrated into the device can affect both the performance of the OSS and the device.

SUMMARY

In accordance with the present principles, a shape sensing enabled instrument includes a flexible longitudinal body including an outer surface which encapsulates interior features. The interior features include an optical fiber lumen configured to receive one or more optical fibers for optical shape sensing, and a mechanical member forming a hollow lumen extending longitudinally down the body. The mechanical member is configured to receive the optical fiber lumen therein to permit rotation and translation of an optical fiber and to protect the optical fiber.

A shape sensing system includes a shape sensing enabled medical instrument having a flexible longitudinal body including an outer surface which encapsulates interior features. The interior features include an optical fiber lumen configured to receive one or more optical fibers for optical shape sensing and a mechanical member forming a hollow extending longitudinally down the body. The mechanical member is configured to receive the optical fiber lumen therein to permit rotation and translation of an optical fiber and to protect the optical fiber. A console is configured to receive optical signals from the one or more optical fibers and interpret the optical signals to determine a shape of the instrument.

A method for sensing a shape in a shape sensing enabled instrument includes providing a flexible longitudinal body including an outer surface which encapsulates interior features, the interior features including an optical fiber lumen configured to receive one or more optical fibers for optical shape sensing and a mechanical member forming a hollow extending longitudinally down the body, the mechanical member configured to receive the optical fiber lumen therein to permit rotation and translation of an optical fiber and to protect the optical fiber; receiving optical signals from the one or more optical fibers; and interpreting the optical signals to determine a shape of the instrument.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
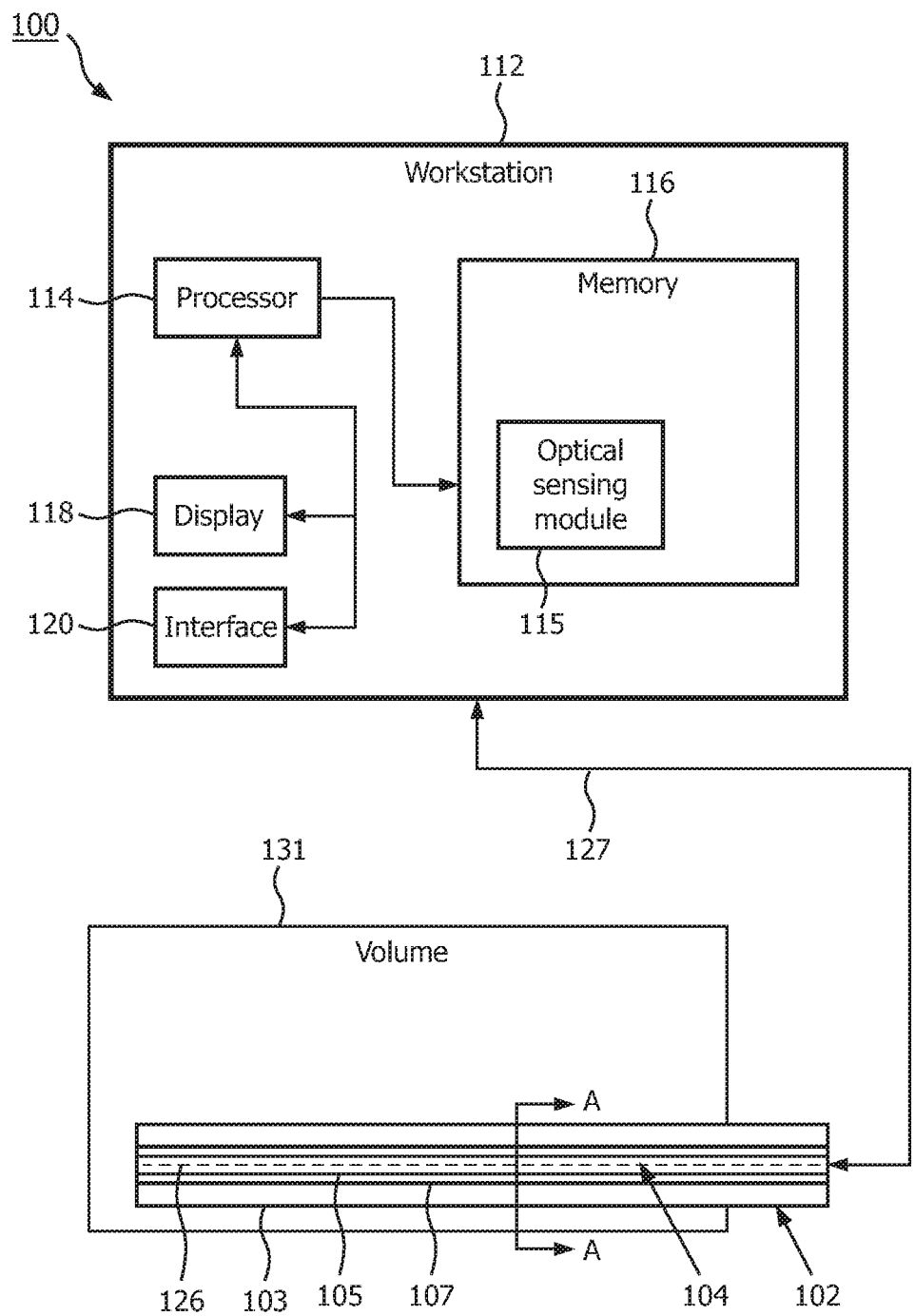
FIG. 1 is a block/flow diagram showing a shape sensing system which employs a mechanical member for receiving a fiber lumen or channel therein in accordance with one embodiment.

In accordance with the present principles, an optical fiber carrying lumen is configured to improve shape sensing performance by dampening vibrations from an external environment, providing a smooth, continuous and pinch-free lumen, and permitting the fiber to slide freely within the lumen. Shape sensing performance can also be improved by decoupling torque of the device from the twisting of the fiber.

In accordance with the present principles, a multi-purpose lumen design is employed for interventional devices that resolve at least three challenges in fiber integration. These include limited cross-sectional area available in the device, protection and isolation of the fiber from the external environment, and decoupling of external torqueing from fiber twist.

Limited cross-sectional area is available inside many interventional devices. A significant challenge is presented to create an optimal lumen for a fiber given the limited space available in the cross-sectional footprint of interventional devices. For example, fiber dimensions are on the order of hundreds of microns on an outer diameter. In many cases, interventional devices include a guide-wire channel, one or multiple support rods, structural braiding and pull wires (in the case of actuated devices) within a small cross-sectional area (e.g., about 2.1 mm in the case of a 6 French catheter).

Present embodiments overcome this space limitation by configuring existing features of medical devices to create a lumen for the optical shape sensing fiber. In some cases, the optical shape sensing performance improves with a larger diameter lumen.

Protection and isolation from the external environment are needed in an OSS, which employs a calculation of strain along a multicore optical fiber to reconstruct the shape along the fiber. As such, the shape stability and reconstruction accuracy are susceptible to changes in tension, twist, vibration, and pinching. Integrating this technology into interventional devices used in a dynamic environment, such as that of vascular navigation, can cause significant degradation of OSS performance due to at least the following effects: 1) longitudinal stick-slip behavior (tension) due to friction between the shape sensing fiber and the lumen wall during curvature induced path length changes; and 2) rotational stick-slip due to friction between the fiber and the lumen wall during torqueing of the device; 3) pinching of the fiber due to ovalization of the lumen due to bending of the device to accommodate the anatomy; 4) vibration due to wall scraping of the tip of the device, clinician handling of the instrument, blood flow around the device, heart beat motion, etc.

The lumen that includes the optical fiber within the device needs to be carefully designed to reduce the negative effects of vibration, pinching, twisting and friction on the fiber. An optimal lumen for the optical shape sensing fiber preferably includes a large lumen diameter; a structured lumen cross-section for reduction of lumen ovalization during bending, vibration dampening effects and a continuous lumen with no transitions or pinch points.

With regard to decoupling of twist, the accuracy of the optical shape sensing position degrades with increased twist along the length of the sensor. Since torqueing of medical instruments is common in many procedures, there is considerable value in designing devices to decouple or reduce the torqueing of the device from twisting of the sensors. With careful selection of the lumen position and properties, it is possible to decouple the instrument torqueing from the twisting of the fiber.

It should be understood that the present invention will be described in terms of medical instruments; however, the teachings of the present invention are much broader and are applicable to any fiber optic instruments. In some embodiments, the present principles are employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W), Blu-Ray™ and DVD.

Referring now to the drawings in which like numerals represent the same or similar elements and initially to FIG. 1, a system 100 for using shape sensing enabled devices is illustratively shown in accordance with one embodiment. System 100 may include a workstation or console 112 from which a procedure is supervised and/or managed.

Workstation 112 preferably includes one or more processors 114 and memory 116 for storing programs and applications. Memory 116 may store an optical sensing module 115 configured to interpret optical feedback signals from a shape sensing medical instrument 104. Optical sensing module 115 is configured to use/interpret the optical signal feedback (and any other feedback, e.g., electromagnetic (EM) tracking) to reconstruct deformations, deflections and other changes associated with a medical device or optical shape sensing enabled medical device 102 and/or its surrounding region. The optical shape sensing enabled medical device 102 may include a catheter, a guidewire, a probe, an endoscope, a robot, an electrode, a filter device, a balloon device, or other medical component, etc.

The present principles reconfigure existing structures in the optical shape sensing enabled medical device 102 to integrate a fiber for optical shape sensing. Specifically, placing the optical sensor inside of the support rods or pull wires within a device not only optimizes the use of the available cross section, but can also provide a suitable lumen for the fiber that will dampen vibration, have structural support to prevent ovalization and pinching of the fiber, and can provide more room for the fiber (thereby increasing the diameter for the lumen including the optical sensor). In some cases the fiber can be rotationally isolated from external torqueing through a multi-purpose design of the lumen.

The shape sensing enabled instrument 104 includes a flexible longitudinal body 103 including an outer surface which encapsulates interior features. The interior features include an optical fiber lumen 105 configured to receive one or more optical fibers for optical shape sensing, and a mechanical member 107 forming a hollow extending longitudinally down the body. The mechanical member 107 is configured to receive the optical fiber lumen therein to permit rotation of an optical fiber and to protect the optical fiber.

The shape sensing enabled medical instrument 104 on optical shape sensing enabled medical device 102 includes one or more optical fibers 126 which are coupled to the optical shape sensing enabled medical device 102 in a set pattern or patterns. The optical fibers 126 connect to the workstation 112 through cabling 127. The cabling 127 may include fiber optics, electrical connections, other instrumentation, etc., as needed.

Shape sensing enabled medical instrument 104 with fiber optics may be based on fiber optic Bragg grating sensors. A fiber optic Bragg grating (FBG) is a short segment of optical fiber that reflects particular wavelengths of light and transmits others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

A fundamental principle behind the operation of a fiber Bragg grating is Fresnel reflection at each of the interfaces where the refractive index is changing. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optical sensors. In an FBG sensor, the measurand (e.g., strain) causes a shift in the Bragg wavelength.

One advantage of this technique is that various sensor elements can be distributed over the length of a fiber. Incorporating three or more cores with various sensors (gauges) along the length of a fiber that is embedded in a structure permits a three dimensional form of such a structure to be precisely determined, typically with better than 1 mm accuracy. Along the length of the fiber, at various positions, a multitude of FBG sensors can be located (e.g., 3 or more fiber sensing cores). From the strain measurement of each FBG, the curvature of the structure can be interred at that position. From the multitude of measured positions, the total three-dimensional form is determined.

As an alternative to fiber-optic Bragg gratings, the inherent backscatter in conventional optical fiber can be exploited. One such approach is to use Rayleigh scatter in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in three or more cores running within a single length of multi-core fiber, the 3D shape and dynamics of the surface of interest can be followed.

In one embodiment, workstation 112 receives feedback from the shape sensing enabled medical instrument 104, and position data as to the location, position/rotation (shape) of the shape sensing enabled medical instrument 104 is provided within a volume 131 (e.g., a patient). An image of the shape sensing enabled medical instrument 104 within the space or volume 131 can be displayed on a display device 118. Workstation 112 includes the display device 118 for viewing internal images of a subject (patient) or volume 131 and may include the image as an overlay or other rendering of the shape sensing enabled medical instrument 104. Display device 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

Figure 3:
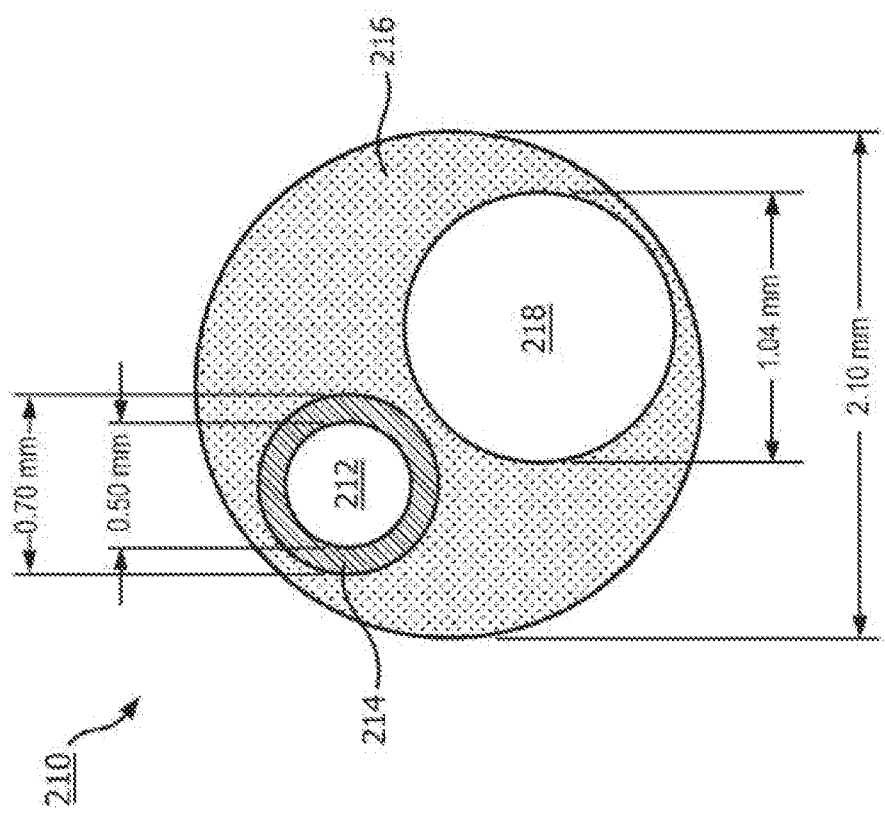
FIG. 3 is a cross-sectional view of a shape sensing enabled catheter having a fiber lumen in a hollow support member in accordance with another embodiment.
Figure 2:
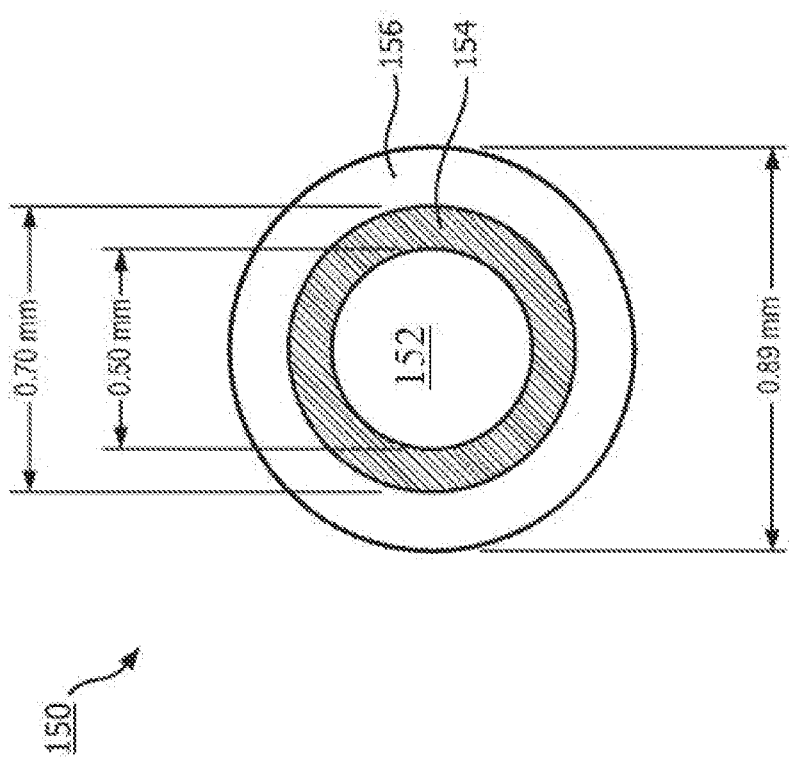
FIG. 2 is a cross-sectional view of a shape sensing enabled guide wire having a fiber lumen in a support member in accordance with one embodiment.
Figure 4:
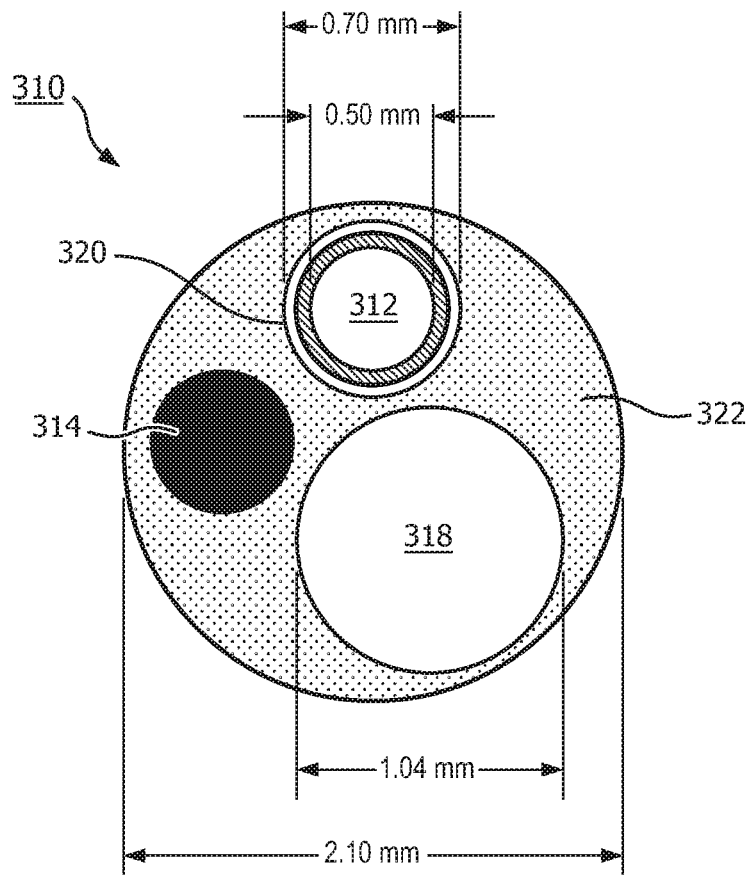
FIG. 4 is a cross-sectional view of a shape sensing enabled catheter having a fiber lumen in a hollow pull wire member in accordance with another embodiment.

FIGS. 2, 3 and 4 show cross-sectional views of different shape sensing enabled medical instruments 104 taken, e.g., at section line A-A. The FIGS. 2, 3 and 4 show some illustrative dimensions provided for comparison. The instruments and devices described herein should not be construed as being limited by these dimensions.

Referring to FIG. 2, a cross-sectional view of a guide wire 150 with an optical fiber channel 152 and a guide wire support rod 154 is illustratively shown in accordance with one embodiment. An optical shape sensing fiber can be included in the optical fiber a 152 of the guide wire 150, which is located inside the guide wire_support rod 154 within the guide wire 150. In such a device, the purpose of the guide wire_support rod 154 is to transmit torque applied by an operator from a proximal end to a distal tip of the guide wire 150. Instead of providing a separate lumen for each component of the device, the guide wire support rod 154 can be employed as the lumen for the optical fiber. Many advantages are achieved with such a design.

For example, the design provides more space for both the guide wire_support rod 154 and the optical fiber channel or lumen 152. Also, the fiber in the fiber channel 152 is now encased within a hollow rod of the guide wire support rod 154, which may include, e.g., NiTi, a steel alloy, or similar material. The guide wire support rod 154 provides a protective environment that can resist pinching and kinking. With some design considerations, this guide wire support rod 154 can also be made to dampen vibration and can be fabricated to minimize friction on its inner surface. Such considerations may include the addition of coatings on the inner diameter of the guide wire support rod 154. These coatings may include Teflon™, PTFE, MDX, Pebax™, or other substances to reduce friction. The guide wire support rod 154 or mechanical member may include at least one of strands, braids, dampening materials, etc. configured to provide vibration-dampening features. The guide wire support rod 154 or mechanical member may be vibrationally damped by being coiled, braided, made from materials with dampening properties, etc.

Another benefit of the multi-purposed design is that the optical fiber now lies along a center of the device 150 (neutral axis), which means that there will be minimal path length changes along the fiber during bending of the device (thereby reducing the amount of motion, friction, and strain that the fiber experiences during bending). In addition, since the fiber lies within the torqueing element of the device and along a central axis, it is rotationally free to slide in the lumen of the guide wire_support rod 154 and will be isolated from external torqueing, unlike the case where the fiber is off-axis where torqueing of the device will necessarily cause the fiber to twist as it is offset from the axis of rotation.

One embodiment may be implemented with only the guide wire_support rod 154 and the lumen 152 for the optical fiber. In another embodiment, a covering 156 (e.g., a Pebax™ covering) may be employed over the guide wire support rod 154.

Referring to FIG. 3, another example shows, in cross-section, an optical fiber channel or lumen 212 for an optical shape sensing fiber within a support rod 214 of a catheter 210. The catheter 210 includes a working channel 218 employed for passing tools or instruments therethrough. Instead of providing a separate lumen for each component of the device, the support rod 214 can also be employed as the lumen 212 for the optical fiber. Advantages of this design include the following. The design provides more space for both the support rod 214 and the optical fiber channel 212. In addition, the fiber is now encased within a hollow rod (support rod 214), which may include, e.g., NiTi, a steel alloy, or similar materials. The hollow support rod 214 provides an optimal environment that can resist pinching and kinking. The support rod 214 can also be made to dampen vibration and can be fabricated to minimize friction on its inner surface (e.g., by adding a coating or coatings in the inner diameter of the support rod 214).

With some design considerations, the support rod 214 can also be made to dampen vibration and can be fabricated to minimize friction on its inner surface. Such considerations may include the addition of coatings on the inner diameter of the support rod 214. These coatings may include Teflon™, PTFE, MDX, Pebax™, or other substances to reduce friction. The support rod 214 or mechanical member may include at least one of strands, braids, dampening materials, etc. configured to provide vibration-dampening features. The support rod 214 or mechanical member may be vibrationally damped by being coiled, braided, made from materials with dampening properties, etc.

An added benefit of the multi-purpose design of FIG. 3 is that the optical fiber now lies largely along the torqueing central axis of the device, so that it is now possible to decouple the torqueing of the device from twisting of the optical fiber. This is relevant because the accumulation of twist in the shape sensing fiber can cause degradation in performance. A covering or filler material 216 (e.g., Pebax™) may be employed over the support rod 214 and to form the working channel 218.

Referring to FIG. 4, an example of a lumen or optical fiber channel 312 for the optical shape sensing fiber is included within a pull wire 320 of a catheter 310. Instead of providing a separate channel for each component of the catheter 310, the pull wire 320 can also be used as the lumen 312 for the optical fiber. The advantages to this design include providing more space for both the pull wire 320 and the optical fiber channel 312 then would have been available for each feature employed separately. Within the pull wire 320, the fiber is now encased within a hollow metal (or other material) lumen, which provides an optimal environment that can resist pinching and kinking. The pull wire 320 can also be made to dampen vibration and can be fabricated to minimize friction on its inner surface.

With some design considerations, the pull wire 320 can also be made to dampen vibration and can be fabricated to minimize friction on its inner surface. Such considerations may include the addition of coatings on the inner diameter of the pull wire 320. These coatings may include Teflon™, PTFE, MDX, Pebax™, or other substances to reduce friction. The pull wire 320 or mechanical member may include at least one of strands, braids, dampening materials, etc. configured to provide vibration-dampening features. The pull wire 320 or mechanical member may be vibrationally damped by being coiled, braided, made from materials with dampening properties, etc.

In another embodiment, a catheter 310 may utilize one or more hollow pull-wires to actuate the catheter 310 in more than one degree of freedom. A support rod 314 and a working channel 318 may also be included. A covering or filler material 322 (e.g., Pebax™) may be employed over the pull wire 320 and to form the working channel 318.

In accordance with other embodiments, a catheter conductive element such as a wire, a lead, a core of an electrophysiology (EP) ablation catheter, etc. may be employed as a hollow rod similar to the embodiments above wherein the optical fiber is included within the conductive element of the catheter. It should be understood that the present embodiments are not limited to a single sensing fiber. Multiple sensing fibers can be included within multiple pull wires or channels within the instrument, or multiple fibers may be included within a single pull wire or channel within the instrument. The multiple sensing fibers may be used for sensing shape, strain, temperature, flow, etc.

The present principles apply to any integration of optical shape sensing sensors into medical devices including manual catheters, actuated catheters (both manual and robotic), guide wires, stylets, endoscopes and bronchoscopes, ultrasound probes, etc. or any other guided devices (medical or non-medical).

Figure 5:
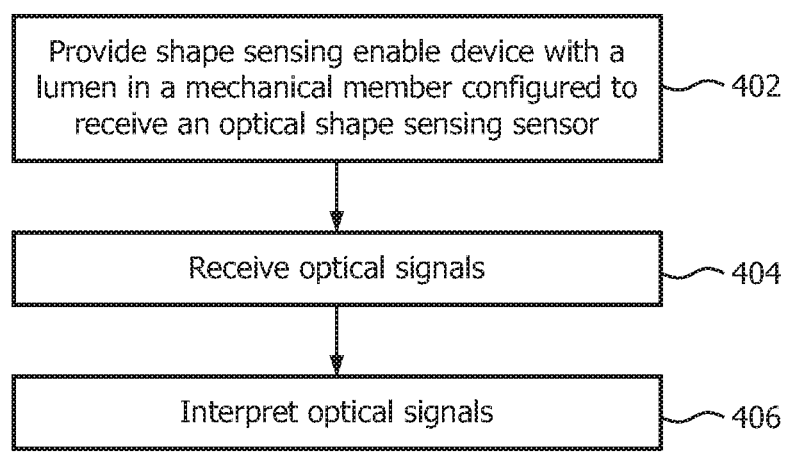
FIG. 5 is a block/flow diagram showing a method for sensing a shape in a shape sensing enabled instrument in accordance with an illustrative embodiment.

Referring to FIG. 5, a method for sensing a shape in a shape sensing enabled instrument is illustratively shown. In block 402, a shape sensing enabled instrument is provided. The shape sensing enabled instrument includes a flexible longitudinal body having an outer surface which encapsulates interior features, the interior features including an optical fiber lumen configured to receive one or more optical fibers for optical shapes sensing and a mechanical member forming a hollow extending longitudinally down the body, the mechanical member configured to receive the optical fiber lumen therein to permit rotation of an optical fiber and to protect the optical fiber. In block 404, optical signals are received from the one or more optical fibers. In block 406, the optical signals are interpreted to determine a shape of the instrument.

In interpreting the appended claims, it should be understood that:
a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for multipurpose lumen designs for optical shape sensing (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims, Having thus described the details and particularity required by the patent laws, what is claimed and desired protected by Letters Patent is set forth in the appended claims.

The invention claimed is:

1. A shape sensing enabled instrument, comprising:
   a guide wire comprising an outer surface which encapsulates interior features; the interior features comprising:
   an optical fiber lumen configured to receive one or more optical fibers for shape sensing;
   a guide wire support rod configured to receive the optical fiber lumen therein to permit rotation and translation of the one or more optical fibers and to protect the one or more optical fibers, wherein: the optical fiber lumen substantially decouples torqueing of the instrument from twisting the one or more optical fibers, which are rotationally isolated from external torqueing; and the one or more optical fibers are disposed along a central longitudinal axis of the guide wire; and
   an optical shape sensing fiber disposed within a pull wire.

2. A shape sensing system, comprising:
   a shape sensing enabled medical instrument comprising a guide wire including an outer surface which encapsulates interior features;
   the interior features comprising:
   an optical fiber lumen configured to receive one or more optical fibers for optical shape sensing;
   a guide wire support rod configured to receive the optical fiber lumen therein to permit rotation and translation of the one or more optical fibers,
   wherein: the optical fiber lumen substantially decouples torqueing of the medical instrument from twisting the one or more optical fibers, which are rotationally isolated from external torqueing; and the one or more optical fibers are disposed along a central longitudinal axis of the guide wire;
   an optical shape sensing fiber disposed within a pull wire; and
   a console configured to receive optical signals from the one or more optical fibers and interpret the optical signals to determine a shape of the medical instrument.

3. A method for sensing a shape in a shape sensing enabled instrument, comprising:
   providing a guide wire comprising:
   an outer surface which encapsulates interior features, the interior features including an optical fiber lumen configured to receive one or more optical fibers for optical shape sensing; and a guide wire support rod configured to receive the optical fiber lumen therein to permit rotation and translation of the one or more optical fibers and to protect the one or more optical fibers,
   wherein: the optical fiber lumen substantially decouples torqueing of the instrument from twisting the one or more optical fibers, which are rotationally isolated from external torqueing; and
   the one or more optical fibers are disposed along a central longitudinal axis of the guide wire,
   an optical shape sensing fiber disposed within a pull wire;
   the guide wire support rod comprising an internal coating disposed on an inner diameter thereof, the internal coating being adapted to reduce friction of one or more optical fibers disposed in the guide wire support rod;
   receiving optical signals from the one or more optical fibers; and
   interpreting the optical signals to determine a shape of the instrument.

4. The method as recited in claim 3, wherein the internal coating is further adapted to reduce vibrations in the one or more optical fibers.

5. The shape sensing enabled instrument as recited in claim 1, further comprising an internal coating disposed on an inner diameter of the guide wire support rod, the internal coating being adapted to reduce friction of the one or more optical fibers disposed therein.

6. The shape sensing enabled system as recited in claim 2, further comprising an internal coating disposed on an inner diameter of the guide wire support rod, the internal coating being adapted to reduce friction of the one or more optical fibers disposed therein.

7. The shape sensing enabled instrument of claim 1, wherein the guide wire further comprises at least one of strands and braids configured to provide vibration-dampening features.

8. The shape sensing system of claim 2, wherein the guide wire support rod further comprises at least one of strands and braids configured to provide vibration-dampening features.

9. A shape sensing enabled instrument, comprising:
   a guide wire including an outer surface which encapsulates interior features;
   the interior features comprising:
   an optical fiber lumen configured to receive one or more optical fibers for shape sensing;
   a guide wire support rod comprising at least one of strands, braids, and dampening materials configured to provide vibration-dampening features, wherein the guide wire support rod is configured to receive the optical fiber lumen therein to permit rotation and translation of the one or more optical fibers and to protect the one or more optical fibers, wherein: the optical fiber lumen substantially decouples torqueing of the instrument from twisting the one or more optical fibers, which are rotationally isolated from external torqueing; and the one or more optical fibers are disposed along a central longitudinal axis of the guide wire; and
   an optical shape sensing fiber disposed within a pull wire.

10. The shape enabled instrument of claim 1, wherein the one or more optical fibers are rotationally isolated from external torqueing.

11. The shape enabled instrument of claim 2, wherein the one or more optical fibers are rotationally isolated from external torqueing.

12. The shape enabled instrument of claim 9, wherein the one or more optical fibers are rotationally isolated from external torqueing.

13. The shape enabled instrument of claim 1, wherein the guide wire support rod prevents ovalization, or pinching, or both, of the optical fiber lumen.

14. The shape enabled instrument of claim 2, wherein the guide wire support rod prevents ovalization, or pinching, or both, of the optical fiber lumen.

15. The shape enabled instrument of claim 9, wherein the guide wire support rod prevents ovalization, or pinching, or both, of the optical fiber lumen.

* * * * *